US006207459B1

United States Patent
Weisheit et al.

(10) Patent No.: US 6,207,459 B1
(45) Date of Patent: Mar. 27, 2001

(54) METHOD FOR THE ANALYSIS OF MEDICAL SAMPLES CONTAINING HAEMOGLOBIN

(75) Inventors: Ralph Weisheit, Weilheim; Lieselotte Schellong, Tutzing, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/147,288

(22) PCT Filed: May 30, 1997

(86) PCT No.: PCT/EP97/02834

§ 371 Date: Nov. 20, 1998

§ 102(e) Date: Nov. 20, 1998

(87) PCT Pub. No.: WO97/45732

PCT Pub. Date: Dec. 4, 1997

(30) Foreign Application Priority Data

May 31, 1996 (DE) .............................. 196 22 089

(51) Int. Cl.$^7$ ................................. G01N 33/72
(52) U.S. Cl. ................ 436/66; 436/86; 436/88; 436/84; 436/71; 356/39
(58) Field of Search ................ 436/66, 71, 86, 436/88, 84; 356/39

(56) References Cited

U.S. PATENT DOCUMENTS

| | | | | |
|---|---|---|---|---|
| 3,310,382 | * | 3/1967 | Kingsley | 23/230 |
| 3,533,749 | * | 10/1970 | Kleiman | 23/230 |
| 3,558,278 | * | 1/1971 | Louderback et al. | 23/230 |
| 5,763,281 | * | 6/1998 | Weisheit | 436/74 |
| 5,945,272 | * | 8/1999 | Segall et al. | 425/1.2 |

FOREIGN PATENT DOCUMENTS

| | | |
|---|---|---|
| 44 27 492 A1 | 2/1996 | (DE) . |
| 2034465 | * 6/1980 | (GB) .............................. G01N/33/27 |

OTHER PUBLICATIONS

O. Sonntag, "Haemolysis as an interference factor in clinical chemistry", Journal of Clinical Chemistry and Clinical Biochemistry, vol. 24, No. 2, 1986, pp. 127–139.

B. Hahn et al., "Polychromatic analysis: new applications of an old technique", Clinical Chemistry, vol. 25, No. 6, 1979, pp. 951–959.

* cited by examiner

*Primary Examiner*—Jill Warden
*Assistant Examiner*—Huan Tran
(74) *Attorney, Agent, or Firm*—Arent Fox Kintner Plotkin & Kahn, PLLC

(57) ABSTRACT

The invention concerns a method for the determination of an analyte in a sample containing free haemoglobin in which the determination is carried out by an optical measurement and the value measured for the analyte concentration is mathematically corrected. This method is in particular suitable for determining the parameters total protein, iron and albumin in a medical sample e.g. in a serum or plasma sample. The correction of the measured value for the analyte concentration is achieved by the steps (a) measuring the blank value of the sample to be analysed, (b) measuring the blank value of a haemoglobin-free reference sample, (c) measuring the uncorrected value for the analyte concentration and (d) correcting the value obtained in step (c) by correlation with the values obtained in step (a) and (b) in order to obtain the corrected value for the analyte concentration.

17 Claims, No Drawings

METHOD FOR THE ANALYSIS OF MEDICAL SAMPLES CONTAINING HAEMOGLOBIN

DESCRIPTION

The invention concerns a method for the determination of an analyte in a sample containing free haemoglobin in which the determination is carried out by an optical measurement and the measured value for the analyte concentration is mathematically corrected. In particular this method is suitable for the determination of the parameters total protein, iron and albumin in a medical sample e.g. in a serum or plasma sample.

It is generally known that haemolysis interferes in some cases to a considerable extent with the determination of numerous analytes. In order to nevertheless obtain measurement values that are not falsified various methods were published in the past for the reduction of haemolysis interference.

As mentioned in the patent EP-0 268 025 B1 a graphical relationship was established for some analytes between the degree of haemolysis and the resulting measurement error. Correction factors could be derived from this which were used to mathematically correct the analytical result obtained on the basis of a separate determination of the degree of haemolysis.

Jay and Provasek also describe that unfalsified values can be obtained in haemolytic samples by determining the degree of haemolysis and using a correction factor (Clin Chem 38/6, 1026 (1992) and Clin Chem 39/9, 1804–1810 (1993)). In this case the degree of haemolysis was determined by a separate measurement of the Hb content in the sample.

In the patent document U.S. Pat. No. 4,263,512 it is recommended that the degree of turbidity (X), haemolysis (Y) and icterus (Z) are determined in addition to the analyte and that the measured analyte value (S) is corrected with the aid of the formula $S'=S-\alpha.X-\beta.Y\gamma.Z$. In this case $S'$ is the corrected analyte value and $\alpha$, $\beta$ and $\gamma$ are correction factors which were obtained by measuring the influence of turbidity, haemolysis and icterus by means of reference liquids. X, Y and Z are determined by multichannel measurement and a subsequent complicated calculation from the absorbance differences obtained taking into consideration the respective proportion of the other interfering substances.

One method of correcting haemolysis interferences without a separate determination of the degree of haemolysis is shown by DE 44 27 492 A1. Here a mathematical relation was found between the content of interfering substance released by haemolysis from the erythrocytes and a pre-reaction which occurs before the main reaction. The analytical result obtained in the main reaction (rate $_{total}$) can be corrected with the aid of the degree of haemolysis determined in this way during the pre-reaction utilizing the relation found between the degree of haemolysis and interference contribution according to the formula $rate_{substance/sample} = rate_{total} - rate_{pre-reaction} - rate_{substance/erythrocyte}$, in which substance means the component to be determined in the sample.

Frequently an interference by haemoglobin can also be eliminated by measuring the sample blank value. This, however, does not apply to the determination of total protein by means of the Biuret method (Morgan et al., Microchem. J. 44, 282–287 (1991)) and also not to the determination of albumin by means of the bromocresol-green and bromocresol-purple method. Furthermore it is known that interferences by haemoglobin always occur in the determination of iron if Hb has not previously been removed from the sample by dialysis (Sonntag, J.Clin. Chem. Clin. Biochem. 24/2, 127–139 (1986)). Also in the case of iron it is not possible to eliminate the Hb interference by the sole measurement of the sample blank value.

However, all the methods for eliminating interference described above have the disadvantage that they involve a considerable amount of work (sample preparation by dialysis or the separate determination of the degree of haemolysis e.g. by determining the Hb content) and/or complicated mathematical correction algorithms.

In addition the described methods all relate to the elimination of erroneous measurements caused by haemolysis. The development of blood substitutes based on haemoglobin has made the issue of removing interferences by native or synthetic haemoglobin or haemoglobin-like compounds even more critical than before. Such interference then also on the one hand occur in non-haemolytic sample material and on the other hand also to a much greater extent than in the case of native haemolysis since in blood substitute treatment the haemoglobin content in blood serum or plasma can be more than 1000 mg/dl.

The object of the present invention was to provide a method for the elimination of interferences which are caused by native haemoglobin or blood substitutes based on synthetic Hb or Hb-like compounds and which cannot be eliminated by the simple measurement of the sample blank value. In addition this method should be associated with a significantly reduced work load compared to conventional methods and guarantee an elimination of interference up to at least 1000 mg/dl Hb.

The object of the invention was achieved in that surprisingly a relation was found between the level of the sample blank value and the degree of the falsification of the measured results caused by free haemoglobin. As a result it is possible with the aid of a simple mathematical correction formula to exactly determine the correct value for the analyte concentration even when the Hb content is high. In comparison to the state of the art the method according to the invention is advantageously characterized in that neither a separate determination of the Hb content nor a determination of the degree of a pre-reaction are necessary in order to correct the measured value of a medical sample containing Hb.

Hence a subject matter of the present invention is a method for the determination of an analyte in a sample containing free haemoglobin by optical measurement wherein the measured value for the analyte concentration is corrected by the steps:

(a) measuring the blank value of the sample to be analysed, (b) measuring the blank value of a haemoglobin-free reference sample, (c) measuring the uncorrected value for the analyte concentration and (d) correcting the value obtained in step (c) by correlation with the values obtained in step (a) and (b) in order to obtain the corrected value for the analyte concentration.

The corrected value for the analyte concentration in step (d) of the method according to the invention is preferably determined according to the following relationship:

$$C'_{sample} = C_{sample} - FE1_{sample} + FE1_{reference}$$

in which
- $C'_{sample}$ is the corrected value for the analyte concentration,
- $C_{sample}$ is the uncorrected measured value for the analyte concentration in the sample,
- F is a test-specific correction factor,
- $E1_{sample}$ is the measured blank value in the sample and
- $E1_{reference}$ is the measured blank value in the reference sample.

The correction method according to the invention is suitable for methods in which the analyte is determined by optical measurement in particular at wavelengths at which an interference by free haemoglobin present in the sample occurs. The optical measurement is particularly preferably carried out in the range of 500–750 nm.

The method according to the invention is suitable for the determination of any samples in which free haemoglobin is present. Examples of such samples are haemolytic serum or plasma samples or samples which contain a blood substitute. Examples of blood substitutes which fall under the term "free haemoglobin" within the sense of the present invention are derivatized, polymerized, modified or cross-linked derivatives of haemoglobins, in particular of human haemoglobin or bovine haemoglobin as well as recombinantly produced haemoglobin.

In a preferred embodiment of the method according to the invention the total protein content of the sample is determined. This determination is preferably carried out according to the Biuret method. In a further particularly preferred embodiment of the present invention the iron content of the sample is determined. This determination of the iron content is preferably carried out according to the ferrozine method. In yet a further particularly preferred embodiment the albumin content of a sample is determined. This determination of the albumin content is preferably carried out according to the bromocresol-green or bromocresol-purple method. The measurement procedure for the determination of these parameters in which no simple method of eliminating interference in the determination of samples containing haemoglobin was previously known can be surprisingly simplified by the method according to the invention.

A further feature of the method according to the invention is that it is even possible to easily measure icteric samples with a high content of bilirubin up to at least 20 mg/dl. An interference by lipaemic samples can be eliminated by using an appropriate clearing agent which for example is added to the reagent.

A serum or plasma sample and in particular a human serum or plasma sample is preferably used as the sample in the method according to the invention. Serum or plasma samples from clinically healthy test persons are advantageously used as reference samples. It is particularly preferable to use a haemoglobin-free serum or plasma pool from clinically healthy test persons.

A particular advantage of the method according to the invention is that it can be carried out on an automated analyzer e.g. on a Boehringer Mannheim/Hitachi 704 or 717 analyzer. Due to the simple mathematical correction formula the automated analyzer can be programmed in such a way that the output is already the corrected value for the analyte concentration and a subsequent mathematical correction is no longer necessary.

An important parameter for the correction of the measured analyte concentration is the test-specific correction factor F. This correction factor F is preferably determined by a procedure which comprises the steps:

(a) Preparing a series of at least three samples with the same content of analyte of which at least one of the samples contains no haemoglobin and at least two of the samples contain different concentrations of free haemoglobin, (b) measurement of the blank value of each sample in which the increase of the sample blank value caused by the presence of haemoglobin compared to the haemoglobin-free sample is determined, (c) measuring the uncorrected analyte concentration in each sample in which the falsification of the measured value caused by the presence of haemoglobin compared to the haemoglobin-free reference sample is determined and (d) the falsification of the measured value determined in step (c) is correlated with the increase of the sample blank value determined in step (b) in order to obtain the test-specific correction factor.

When determining the correction factor F it is preferable to prepare a series of samples of which at least 5 and for example 10 of the samples contain different concentrations of free haemoglobin. The concentrations of free haemoglobin are for example varied for the sample series in the range of 0 mg/dl up to at least 1000 mg/dl.

For a particular sample from the series containing free haemoglobin a sample-specific correction factor F' is determined according to the following relationship:

$$F' = \Delta C : \Delta E1$$

in which:
- $\Delta C$ is the amount of the falsification of the measured value compared to the reference sample caused by the presence of free haemoglobin for each sample and
- $\Delta E1$ is the increase of the sample blank value compared to the reference sample caused by the presence of free haemoglobin for each sample.

The test-specific correction factor F can be determined by calculating the mean of the correction factors F' determined for the respective samples. In this manner it was possible to determine a correction factor F of 0.332 for the albumin test by the bromocresol-green method, a correction factor F of 0.290 for the iron test by the ferrozine method and a correction factor of 0.115 for the total protein test by the Biuret method. When these correction factors are used an excellent recovery rate of the analyte to be determined is found in samples containing haemoglobin.

The invention is further elucidated by the following examples:

General methods

1. Determination of the correction factor (cf also examples 1–3)

From a serum or plasma pool of clinically healthy test persons 11 samples are spiked with different amounts of haemolysate, haemoglobin or a Hb-like compound in such a way that, at a constant analyte content, a Hb concentration series is formed the lowest sample of which (=reference) contains no Hb and the highest sample of which contains at least 1000 mg/dl Hb. All samples of this series are measured with the respective test to obtain a falsified analyte value compared to the reference for each sample depending on its Hb content.

For each sample the increase of the sample blank value $\Delta E1$ caused by Hb compared to the sample blank value of the Hb-free sample (=reference) is determined: $\Delta E1 = E1_{sample} - E1_{reference}$.

In addition the amount of falsification $\Delta C$ of the analyte value caused by Hb compared to the analyte value measured in the reference is determined for each sample: $\Delta C = C_{sample} - C_{reference}$.

When the interfering component $\Delta C$ is divided by the value of the sample blank value increase $\Delta E1$ a correction factor is obtained for each sample $F'_{sample} = \Delta C : \Delta E1$.

The mean correction factor F is then calculated from the 10 individual factors of the Hb concentration series obtained in this manner. This factor is a fixed parameter which only has to be determined once for albumin, iron and total protein and which is then, however, constant for the respective test.

2. Calculation of the corrected analyte value (cf also examples 4–8)

The corrected and hence the analyte value without interference of the respective sample $C'_{sample}$ is determined by mathematical correction of the measured analyte value of the sample $C_{sample}$ by the interference component $\Delta C$.

$C'_{sample} = C_{sample} - \Delta C$
$C'_{sample} = C_{sample} - F \cdot \Delta E$
$C'_{sample} = C_{sample} - F \cdot (E1_{sample} - E1_{reference})$
$C'_{sample} = C_{sample} - F \cdot E1_{sample} + F \cdot E1_{reference}$.

As described above the reference is a Hb-free serum or plasma pool of clinically healthy test persons. For the said methods the influence of the variation range of the measured sample blank values of various patient samples is negligible due to the relation between the sample blank value and measured signal. Even icteric samples with a bilirubin content of at least 20 mg/dl do not interfere. Interference by lipaemic samples can be eliminated by using an appropriate clearing agent which for example is added to the reagent. Icteric and lipaemic samples were prepared by spiking human sera with bilirubin and Intralipid® similarly to Glick (Clin. Chem. 32/3, 470–475 (1986)).

In an analyzer which measures automatically such as e.g. the Boehringer Mannheim/Hitachi 704 or 717 instruments the calculation of the uninterfered analyte value can be programmed in such a way that only the corrected values are printed out and a subsequent mathematical correction is no longer necessary. This programming is for example carried out for albumin on a Boehringer Mannheim/Hitachi 704 instrument as follows:

1. Parameter program: Chemical parameters:

| Test | Test 1 (BLALB) | Test 2 (ALB) |
| --- | --- | --- |
| assay code | 3-15-0 | 3-15-23 |
| sample volume (µl) | 4 | 4 |
| R1 volume (µl) | 350 | 350 |
| R2 volume (µl) | 0 | 350 |

-continued

| Test | Test 1 (BLALB) | Test 2 (ALB) |
| --- | --- | --- |
| wavelengths | 700–600 | 700–600 |
| calibration | K-factor | 1-0-0 |
| std. (1) conc.-pos (g/l) | 0.00 | 0–1 |
| std. (2) conc.-pos (g/l) | | target value-2 |

2. Monitor: calibration monitor (1): for test 1 enter 0 for S1 absorbance and 100,000 for K.

3. The corrected analyte value is calculated by the calculated test (see Boehringer Mannheim/Hitachi 704 manual)

Calculated test=(test 2)−(test 1)·F+concentration$_{reference}$

Test 2 is the determination of the concentration of the measured uncorrected analyte value, Test 1 is the determination of the absorbance of the sample blank value, F is the factor determined for albumin, iron or total protein to correct the Hb interference Concentration$_{reference}$=F·E1$_{reference}$ and is entered as a concentration.

EXAMPLE 1

Determination of the correction factor for the determination of albumin according to the bromocresol-green method.

The determination was carried out at 37° C. on a Boehringer Mannheim/Hitachi 704 analyzer using the assay code 2-15-23. The following reagents were used:

Reagent 1: 75 mmol/l succinate buffer, pH 4.2

Reagent 2: 75 mmol/l succinate buffer, pH 4.2; 0.3 mmol/l bromocresol-green.

The test procedure was as follows: 350 µl reagent 1 was added to 4 µl sample and after determination of the sample blank value 350 µl reagent 2 was added. Then the analyte was determined after a period of 2 min. A main wavelength of 600 nm and a secondary wavelength of 700 nm were used for the measurement.

The result of this determination is shown in table 1. The value for the test-specific correction factor was determined as 0.332.

EXAMPLE 2

Determination of the correction factor for the determination of iron according to the ferrozine method.

The determination was carried out at 37° C. on a Boehringer Mannheim/Hitachi 717 analyzer using the assay code 2-24-30. The following reagents were used:

Reagent 1: 150 mmol/l Na-acetate buffer, pH 5.0; 4 mmol/l guanidinium chloride; 100 mmol/l thiourea; detergent;

Reagent 2: 150 mmol/l ascorbic acid, 50 mmol/l ferrozine.

The test procedure was as follows: 250 µl reagent 1 was added to 20 µl sample and after determination of the sample blank value 50 µl reagent 2 was added. Then the analyte was determined after a period of 1 min. A main wavelength of 546 nm and a secondary wavelength of 700 nm were used for the measurement.

The result of this experiment is shown in table 2. The value for the test-specific correction factor was determined as 0.290.

EXAMPLE 3

Determination of the correction factor for the determination of total protein according to the Biuret method.

The determination was carried out at 37° C. on a Boehringer Mannheim/Hitachi 717 analyzer using the assay code 2-24-50. The following reagents were used:

Reagent 1: 200 mmol/l NaOH; 32 mmol/l K-Na-tartrate;

Reagent 2: 200 mmol/l NaOH; 32 mmol/l K-Na-tartrate; 30.5 mmol/l KI; 12.15 mmol/l Cu sulfate.

The test procedure was as follows: 250 µl reagent 1 was added to 7 µl sample and after determination of the sample blank value 250 µl reagent 2 was added. Then the analyte was determined after a period of 5 min. A main wavelength of 546 nm and a secondary wavelength of 700 nm were used for the measurement.

The result of this experiment is shown in table 3. The value for the test-specific correction factor was determined as 0.115.

EXAMPLE 4

Use of the correction formula for the albumin determination.

The correction factor determined in example 1 was used to determine samples containing haemoglobin which were obtained by spiking with blood substitutes.

The test procedure was as described in example 1.

The formula to calculate the corrected analyte concentration in the sample was as follows:

$C'_{sample} = C_{sample} - F.E1_{sample} + F.E1_{reference} = C_{sample} - F.E1_{sample} + 0.3$ g/l.

The result of this experiment is shown in Table 4. It can be seen that a recovery rate of 100±1% was achieved by the correction.

EXAMPLE 5

Using the correction formula for the determination of iron

Iron was determined according to the ferrozine method using the correction factor determined in example 2 in samples containing haemoglobin which were obtained by spiking with haemolysate.

The test procedure was as described in example 2.

The formula for calculating the corrected analytical value was as follows:

$C'_{sample} = C_{sample} - F.E1_{sample} + F.E1_{reference} = C_{sample} - F.E1_{sample} + 2.9$ µg/dl.

The result of this experiment is shown in Table 5. It can be seen that an excellent recovery of iron was achieved which, with the exception of a single value, was in the range of 100%±2.5%.

EXAMPLE 6

Use of the correction formula for the determination of total protein

The correction factor determined in example 3 was used to determine total protein according to the Biuret method in samples containing haemoglobin which were obtained by spiking with blood substitutes. The experiment was carried out as described in example 3.

The formula for calculating the corrected analytical value was as follows:

$C'_{sample} = C_{sample} - F.E1_{sample} + F.E1_{reference} = C_{sample} - F.E1_{sample} + 0.6$ g/l.

The result of the experiments is shown in Table 6. It can be seen that the recovery for total protein was in most cases in the range of 100±1%.

EXAMPLE 7

Determination of albumin in icteric samples

The test-specific correction factor determined in example 1 was used to determine albumin according to the bromocresol-green method in icteric samples which were obtained by spiking with bilirubin.

The test procedure was as described in example 1. The formula for calculating the corrected analytical value was as described in example 4.

The result of this experiment is shown in Table 7. It can be seen that the use of the correction formula did not lead to a worsening of the recovery.

EXAMPLE 8

Determination of iron in lipaemic samples

The test-specific correction factor determined in example 2 was used to determine iron according to the ferrozine method in lipaemic samples which were obtained by spiking with Intralipid®.

The test procedure was as described in example 2. The formula for calculating the corrected analytical value was as given in example 5.

The result of the experiment is shown in Table 8. It can be seen that the use of the correction formula does not lead to a worsening of the recovery in lipaemic samples.

TABLE 1

| Sample No. | Hb content [mg/dl] | E1 sample [mA] | delta E1 [mA] | C sample (= measured values) [g/l] | delta C [g/l] | F sample [g/l] |
|---|---|---|---|---|---|---|
| 1 (= reference) | 0 | 1.0 | — | 32.4 | — | — |
| 2 | 200 | 6.8 | 5.8 | 34.3 | 1.9 | 0.328 |
| 3 | 400 | 12.5 | 11.5 | 36.1 | 3.7 | 0.322 |
| 4 | 600 | 18.1 | 17.1 | 38.0 | 5.6 | 0.328 |
| 5 | 800 | 23.5 | 22.5 | 40.0 | 7.6 | 0.338 |
| 6 | 1000 | 29.0 | 28.0 | 41.8 | 9.4 | 0.336 |
| 7 | 1200 | 34.5 | 33.5 | 43.8 | 11.4 | 0.340 |
| 8 | 1400 | 39.7 | 38.7 | 45.4 | 13.0 | 0.336 |
| 9 | 1600 | 44.9 | 43.9 | 47.0 | 14.6 | 0.333 |
| 10 | 1800 | 50.4 | 49.4 | 48.7 | 16.3 | 0.330 |
| 11 | 2000 | 56.6 | 55.6 | 50.9 | 18.5 | 0.333 |
| | | | | | | F = 0.332 |

TABLE 2

| Sample No. | Hb content [mg/dl] | E1 sample [mA] | delta E1 [mA] | C sample (= measured values) [µg/dl] | delta C [µg/dl] | F sample [µg/dl] |
|---|---|---|---|---|---|---|
| 1 (= reference) | 0 | 10.1 | — | 80.0 | — | — |
| 2 | 100 | 46.8 | 36.7 | 89.3 | 9.3 | 0.253 |
| 3 | 200 | 75.6 | 65.5 | 99.3 | 19.3 | 0.295 |
| 4 | 300 | 114.0 | 103.9 | 110.3 | 30.3 | 0.292 |
| 5 | 400 | 146.2 | 136.1 | 120.3 | 40.3 | 0.296 |
| 6 | 500 | 180.8 | 170.7 | 129.0 | 49.0 | 0.287 |
| 7 | 600 | 214.0 | 203.9 | 140.0 | 60.0 | 0.294 |
| 8 | 700 | 245.4 | 235.3 | 150.3 | 70.3 | 0.299 |
| 9 | 800 | 280.9 | 270.8 | 157.3 | 77.3 | 0.286 |
| 10 | 800 | 314.4 | 304.3 | 166.7 | 86.7 | 0.285 |
| 11 | 1000 | 340.0 | 329.9 | 183.0 | 103.0 | 0.312 |
| | | | | | | F = 0.290 |

TABLE 3

| Sample No. | Hb content [mg/dl] | E1 sample | delta E1 | C sample (= measured values) [g/l] | delta C [g/l] | F sample [g/l] |
|---|---|---|---|---|---|---|
| 1 (= reference) | 0 | 5.1 | — | 55.2 | — | — |
| 2 | 200 | 21.7 | 16.6 | 57.0 | 1.8 | 0.108 |
| 3 | 400 | 37.8 | 32.7 | 58.6 | 3.4 | 0.104 |
| 4 | 600 | 53.9 | 48.8 | 61.1 | 5.9 | 0.121 |
| 5 | 800 | 70.9 | 65.8 | 63.4 | 8.2 | 0.125 |
| 6 | 1000 | 86.4 | 81.3 | 64.9 | 9.7 | 0.119 |
| 7 | 1200 | 103.4 | 98.3 | 66.9 | 11.7 | 0.119 |
| 8 | 1400 | 120.1 | 115.0 | 68.5 | 13.3 | 0.116 |
| 9 | 1600 | 135.7 | 130.6 | 70.1 | 14.9 | 0.114 |
| 10 | 1800 | 152.9 | 147.8 | 72.4 | 17.2 | 0.116 |
| 11 | 2000 | 167.8 | 162.7 | 73.5 | 18.3 | 0.112 |
| | | | | | | F = 0.115 |

TABLE 4

| | | measured albumin values | | | | corrected albumin values | |
|---|---|---|---|---|---|---|---|
| Sample No. | Hb content [mg/dl] | C sample [g/l] | recovery [%] | E1 sample [mA] | F × E1 sample [g/l] | C' sample [g/l] | recovery [%] |
| | | | | | F = 0.332 g/l | | |
| 1 (= reference) | 0 | 32.4 | — | 1.0 | 0.3* | 32.4 | — |
| 2 | 200 | 34.3 | 105.9 | 6.8 | 2.3 | 32.3 | 99.7 |
| 3 | 400 | 36.1 | 111.4 | 12.5 | 4.2 | 32.2 | 99.4 |
| 4 | 600 | 38.0 | 117.3 | 18.1 | 6.0 | 32.3 | 99.7 |
| 5 | 800 | 40.0 | 123.5 | 23.5 | 7.8 | 32.5 | 100.3 |

TABLE 4-continued

|  | | measured albumin values | | | | corrected albumin values | |
| --- | --- | --- | --- | --- | --- | --- | --- |
| Sample No. | Hb content [mg/dl] | C sample [g/l] | recovery [%] | E1 sample [mA] | F × E1 sample [g/l] | C' sample [g/l] | recovery [%] |
| 6 | 1000 | 41.8 | 129.0 | 29.0 | 9.6 | 32.5 | 100.3 |
| 7 | 1200 | 43.8 | 135.2 | 34.5 | 11.5 | 32.6 | 100.6 |
| 8 | 1400 | 45.4 | 140.1 | 39.7 | 13.2 | 32.5 | 100.3 |
| 9 | 1600 | 47.0 | 145.1 | 44.9 | 14.9 | 32.4 | 100.0 |
| 10 | 1800 | 48.7 | 150.3 | 50.4 | 16.7 | 32.3 | 99.7 |
| 11 | 2000 | 50.9 | 157.1 | 56.6 | 18.8 | 32.4 | 100.0 |
|  |  |  |  |  | *F × E1 reference |  |  |

TABLE 5

|  | | measured iron values | | | | corrected iron values | |
| --- | --- | --- | --- | --- | --- | --- | --- |
| Sample No. | Hb content [mg/dl] | C sample [µg/l] | recovery [%] | E1 sample [mA] | F × E1 sample [µg/dl] | C' sample [µg/dl] | recovery [%] |
|  |  |  |  |  | F = 0.290 µg/dl |  |  |
| 1 (= reference) | 0 | 80.0 | — | 10.1 | 2.9* | 80.0 | — |
| 2 | 100 | 89.3 | 111.6 | 46.8 | 13.6 | 78.6 | 98.2 |
| 3 | 200 | 99.3 | 124.1 | 75.6 | 21.9 | 80.3 | 100.4 |
| 4 | 300 | 110.3 | 137.9 | 114.0 | 33.1 | 80.1 | 100.1 |
| 5 | 400 | 120.3 | 150.4 | 146.2 | 42.4 | 80.8 | 101.0 |
| 6 | 500 | 129.0 | 161.2 | 180.8 | 52.4 | 79.5 | 99.4 |
| 7 | 600 | 140.0 | 175.0 | 214.0 | 62.1 | 80.8 | 101.0 |
| 8 | 700 | 150.3 | 187.9 | 245.4 | 71.2 | 82.0 | 102.5 |
| 9 | 800 | 157.3 | 196.6 | 280.9 | 81.5 | 78.7 | 98.4 |
| 10 | 900 | 166.7 | 208.4 | 314.4 | 91.2 | 78.4 | 98.0 |
| 11 | 1000 | 183.0 | 228.8 | 340.0 | 98.6 | 87.3 | 109.1 |
|  |  |  |  |  | *F × E1 reference |  |  |

TABLE 6

|  | | measured T protein values | | | | corrected T protein values | |
| --- | --- | --- | --- | --- | --- | --- | --- |
| Sample No. | Hb content [mg/dl] | C sample [g/l] | recovery [%] | E1 sample [mA] | F × E1 sample [g/l] | C' sample [g/l] | recovery [%] |
|  |  |  |  |  | F = 0.115 g/l |  |  |
| 1 (= reference) | 0 | 55.2 | — | 5.1 | 0.6* | 55.2 | — |
| 2 | 200 | 57.0 | 103.3 | 21.7 | 2.5 | 55.1 | 99.8 |
| 3 | 400 | 58.6 | 106.2 | 37.8 | 4.3 | 54.9 | 99.5 |
| 4 | 600 | 61.1 | 110.7 | 53.9 | 6.2 | 55.5 | 100.5 |
| 5 | 800 | 63.4 | 114.9 | 70.9 | 8.2 | 55.8 | 101.1 |
| 6 | 1000 | 64.9 | 117.6 | 86.4 | 9.9 | 55.6 | 100.7 |
| 7 | 1200 | 66.9 | 121.2 | 103.4 | 11.9 | 55.6 | 100.7 |
| 8 | 1400 | 68.5 | 124.1 | 120.1 | 13.8 | 55.3 | 100.2 |
| 9 | 1600 | 70.1 | 127.0 | 135.7 | 15.6 | 55.1 | 99.8 |
| 10 | 1800 | 72.4 | 131.2 | 152.9 | 17.6 | 55.4 | 100.4 |
| 11 | 2000 | 73.5 | 133.2 | 167.8 | 19.3 | 54.8 | 99.3 |
|  |  |  |  |  | *F × E1 reference |  |  |

TABLE 7

|  | bilirubin | measured albumin values | | | | corrected albumin values | |
| --- | --- | --- | --- | --- | --- | --- | --- |
| Sample No. | content [mg/dl] | C sample [g/l] | recovery [%] | E1 sample [mA] | F × E1 sample [g/l] | C' sample [g/l] | recovery [%] |
|  |  |  |  |  | F = 0.332 g/l |  |  |
| 1 (= reference) | 0 | 48.3 | — | 0.8 | 0.3* | 48.3 | — |
| 2 | 6 | 47.9 | 99.2 | 0.8 | 0.3 | 47.9 | 99.2 |
| 3 | 13 | 48.0 | 99.4 | 0.9 | 0.3 | 48.0 | 99.4 |

TABLE 7-continued

| | bilirubin | measured albumin values | | | | corrected albumin values | |
|---|---|---|---|---|---|---|---|
| Sample No. | content [mg/dl] | C sample [g/l] | recovery [%] | E1 sample [mA] | F × E1 sample [g/l] | C' sample [g/l] | recovery [%] |
| 4  | 20 | 47.9 | 99.2  | 0.8 | 0.3 | 47.9 | 99.2  |
| 5  | 26 | 48.2 | 99.8  | 0.9 | 0.3 | 48.2 | 99.8  |
| 6  | 33 | 48.2 | 99.8  | 1.4 | 0.5 | 48.0 | 99.4  |
| 7  | 40 | 48.1 | 99.6  | 1.8 | 0.6 | 47.8 | 99.0  |
| 8  | 46 | 48.5 | 100.4 | 1.8 | 0.6 | 48.2 | 99.8  |
| 9  | 53 | 48.8 | 101.0 | 2.0 | 0.7 | 48.4 | 100.2 |
| 10 | 60 | 47.8 | 99.0  | 2.0 | 0.7 | 47.4 | 98.1  |
| 11 | 66 | 48.3 | 100.0 | 2.0 | 0.7 | 47.9 | 99.2  |

TABLE 8

| | intralipid | measured iron values | | | | corrected iron values | |
|---|---|---|---|---|---|---|---|
| Sample No. | content [mg/dl] | C sample [µg/l] | recovery [%] | E1 sample [mA] | F × E1 sample [µg/dl] | C' sample [µg/dl] | recovery [%] |
| | | | | | F = 0.290 µg/dl | | |
| 1 (= reference) | 0 | 82.7 | — | 13.2 | 3.8 | 81.8 | — |
| 2  | 100  | 83.7 | 101.2 | 13.1 | 3.8 | 82.8 | 101.2 |
| 3  | 200  | 84.7 | 102.4 | 13.0 | 3.8 | 83.8 | 102.4 |
| 4  | 300  | 84.3 | 101.9 | 13.2 | 3.8 | 83.4 | 102.0 |
| 5  | 400  | 86.0 | 104.0 | 13.3 | 3.9 | 85.0 | 103.9 |
| 6  | 500  | 81.3 | 98.3  | 13.4 | 3.9 | 80.3 | 98.2  |
| 7  | 600  | 84.3 | 101.9 | 13.6 | 3.9 | 83.3 | 101.8 |
| 8  | 700  | 80.7 | 97.6  | 13.3 | 3.9 | 79.7 | 97.4  |
| 9  | 800  | 86.7 | 104.8 | 13.4 | 3.9 | 85.7 | 104.8 |
| 10 | 900  | 85.3 | 103.1 | 13.4 | 3.9 | 84.3 | 103.1 |
| 11 | 1000 | 82.7 | 100.0 | 13.6 | 3.9 | 81.7 | 99.9  |

We claim:

1. A method for the determination of the concentration of an analyte in a sample containing free haemoglobin by optical measurement wherein the measured value for the analyte concentration is corrected by the steps:

a. optically measuring a blank value of the sample to be analyzed, b. optically measuring a blank value of a haemoglobin-free reference sample, c. adding a reagent to the sample to produce a detectable change in the sample indicative of analyte concentration, d. optically measuring an uncorrected value for the analyte concentration and e. correcting the uncorrected value obtained in step (d) by correlation with the blank values obtained in steps (a) and (b) in order to obtain a corrected value for the analyte concentration, wherein the corrected value for the analyte concentration is calculated according to the following relation:

$$C'_{sample} = C_{sample} - F \cdot E1_{sample} + F \cdot E1_{reference}$$

in which $C'_{sample}$ is the corrected value for the analyte concentration, $C_{sample}$ is the uncorrected measured value for the analyte concentration in the sample, F is a test-specific correction factor, $E1_{sample}$ is the measured blank value in the sample and $E1_{reference}$ is the measured value in the reference sample.

2. Method as claimed in claim 1, wherein the determination of the analyte is carried out by an optical measurement in the range of 600–700 nm.

3. Method as claimed in claim 1, wherein the sample further comprises a blood substitute.

4. Method as claimed in claim 1, wherein the total protein content of the sample is determined.

5. Method as claimed in claim 4, wherein the determination of the total protein content is carried out according to the Biuret method.

6. Method as claimed in claim 1, wherein the iron content of the sample is determined.

7. Method as claimed in claim 6, wherein the iron content is determined according to the ferrozine method.

8. Method as claimed in claim 1, wherein the albumin content of the sample is determined.

9. Method as claimed in claim 8, wherein the albumin content is determined according to the bromocresol-green or the bromocresol-purple method.

10. Method as claimed in claim 1, wherein in the determination of lipaemic samples and prior to step (a) in claim 1 a clearing agent is added.

11. Method as claimed in claim 1, wherein the determination is carried out on a serum or plasma sample.

12. Method as claimed in claim 1, wherein serum or plasma samples of clinically healthy test persons are used to produce the haemoglobin-free reference sample.

13. Method as claimed in claim 1, wherein the method is carried out in an automated analyzer.

14. Method as claimed in claim 1, wherein the determination of the test-specific correction factor F comprises the steps:

(i) Preparing a series of at least three standard samples with the same content of analyte of which at least one of the standard samples contains no haemoglobin and at least two of the standard samples contain different concentrations of free haemoglobin, (ii) measuring a blank value of each standard sample to determine the increase of the standard sample blank value caused by the presence of haemoglobin compared to the haemoglobin-free standard sample, (iii) measuring an uncorrected analyte concentration in each standard sample to determine the falsification of the measured value caused by the presence of haemoglobin compared to the haemoglobin-free standard sample and (iv) the falsification of the measured value determined in step (iii) is correlated with the increase of the standard sample blank value determined in step (iii) in order to obtain the test specific correction factor, F.

15. Method as claimed in claim 14, wherein a series of standard samples is prepared of which at least 5 of the standard samples contain different concentrations of free haemoglobin.

16. Method as claimed in claim 14, wherein a series of samples is prepared the concentration of which varies from 0 mg/dl to at least 1000 mg/dl of free haemoglobin.

17. Method as claimed in claim 14, wherein a sample-specific correction factor F' is determined for a sample containing free haemoglobin according to the following relationship:

$$F' = \Delta C : \Delta E1$$

in which: $\Delta C$ is the amount of the falsification of the measured concentration of analyte compared to the haemoglobin-free analyte reference sample caused by the presence of free haemoglobin for a sample and $\Delta E1$ is the increase of the sample blank value compared to the haemoplobin-free reference sample caused by the presence of free haemoglobin for a sample, and the test-specific correction factor F is determined by calculating the mean of the correction factors F' determined for the respective samples.

* * * * *